United States Patent
Clement et al.

(10) Patent No.: US 9,528,061 B2
(45) Date of Patent: Dec. 27, 2016

(54) SOLUBILIZATION OF COAL OR LIGNOCELLULOSE BIOMASS

(75) Inventors: Brian G. Clement, Houston, TX (US); Toby Richardson, San Diego, CA (US); Stuart A. Underwood, Roanoke, VA (US)

(73) Assignee: Synthetic Genomics Inc., La Jolla, CA (US)

( * ) Notice: Subject to any disclaimer, the term of this patent is extended or adjusted under 35 U.S.C. 154(b) by 524 days.

(21) Appl. No.: 13/229,504

(22) Filed: Sep. 9, 2011

(65) Prior Publication Data

US 2012/0064609 A1 Mar. 15, 2012

Related U.S. Application Data (60) Provisional application No. 61/381,839, filed on Sep. 10, 2010.

(51) Int. Cl.
| | | |
|---|---|---|
| *C10L 3/08* | (2006.01) | |
| *C10G 1/00* | (2006.01) | |
| *C12P 5/02* | (2006.01) | |
| *C13K 1/02* | (2006.01) | |

(52) U.S. Cl.
CPC . *C10L 3/08* (2013.01); *C10G 1/00* (2013.01); *C12P 5/023* (2013.01); *C13K 1/02* (2013.01); *C10G 2300/1014* (2013.01); *C12P 2201/00* (2013.01); *Y02E 50/343* (2013.01); *Y02P 30/20* (2015.11)

(58) Field of Classification Search
None
See application file for complete search history.

(56) References Cited

U.S. PATENT DOCUMENTS

| | | | |
|---|---|---|---|
| 2,081,676 A | | 5/1937 | Neugebauer |
| 3,701,712 A | | 10/1972 | Samuelson et al. |
| 4,050,981 A | | 9/1977 | Jamieson et al. |
| 4,368,922 A | * | 1/1983 | Hemphill et al. ............... 299/5 |
| 4,576,707 A | * | 3/1986 | Siskin ..................... C10G 1/00 |
| | | | 208/430 |
| 4,671,801 A | * | 6/1987 | Burgess et al. ................ 44/280 |
| 6,783,567 B1 | * | 8/2004 | Waters et al. ..................... 71/24 |
| 7,185,702 B2 | | 3/2007 | Blauch et al. |
| 8,459,349 B2 | * | 6/2013 | Downey ........................ 166/246 |

FOREIGN PATENT DOCUMENTS

| | | | |
|---|---|---|---|
| CN | 1562900 | * | 1/2005 |
| CN | 1562900 A | | 1/2005 |
| WO | WO 83/02952 | * | 9/1983 |
| WO | WO 83/02952 A1 | | 9/1983 |

* cited by examiner

*Primary Examiner* — Vera Afremova
(74) *Attorney, Agent, or Firm* — DLA Piper LLP (US)

(57) ABSTRACT

The present methods deal with the solubilization of coal and lignocellulose biomass using pyrophosphates, polyphosphates, or derivatives thereof.

10 Claims, 8 Drawing Sheets

Figure 8

SOLUBILIZATION OF COAL OR LIGNOCELLULOSE BIOMASS

CROSS REFERENCE TO RELATED APPLICATION(S)

This application claims the benefit of priority under 35 U.S.C. §119(e) of U.S. Ser. No. 61/381,839, filed Sep. 10, 2010, the entire content of which is incorporated herein by reference.

FIELD OF THE INVENTION

This invention relates generally to the conversion of coal and lignocellulose biomass to solubilized products.

BACKGROUND OF THE INVENTION

Coal is a relatively insoluble, complex solid polymer. Thermal and chemical processes for the conversion of coal to liquid and gaseous products generally require somewhat extreme temperature, pressure and chemical conditions. The severity of the operating conditions may commonly include pressures in excess of 3,000 psi and temperatures in excess of 800 degrees Fahrenheit. These processes usually also require a significant capital investment.

SUMMARY OF THE INVENTION

It is an object of the present methods to provide for the solubilization or liquefaction of coal or lignocellulose biomass via exposure to a pyrophosphate or a polymer of phosphate.

It is a further object of the present invention to provide a means to accomplish coal solubilization in a subterranean formation. The present methods comprise depolymerizing a solid coal matrix into soluble, coal-derived constituents.

The foregoing methods are accomplished in accordance with the present invention, generally speaking, by providing a method for contacting coal or lignocellulosic material with a composition comprising a pyrophosphate or a derivative thereof. Solubilization of coal can be carried out in a subterranean formation, in a terrestrial formation or in an ex situ reactor under conditions which include introducing a composition comprising a pyrophosphate or a derivative thereof to coal so as to cause solubilization of the coal.

Pyrophosphates contemplated herein include, but are not limited to, sodium pyrophosphate ($NaP_2O_7$), calcium pyrophosphate ($Ca_2P_2O_7$), potassium pyrophosphate ($K_4P_2O_7$), ferrous pyrophosphate, ferric pyrophosphate, pyrophosphoric acid, or a derivative thereof.

Derivatives include, but are not limited to, hexametaphosphate, sodium tripolyphosphate, disodium pyrophosphate; dicalcium pyrophosphate, dipotassium pyrophosphate, tetrasodium pyrophosphate, tetracalcium pyrophosphate or tetrapotassium pyrophosphate.

In one aspect, the compositions further comprise one or more oxidants.

In another aspect, the methods further comprise contacting solubilized coal with one or more microorganisms, one or more consortiums, one or more functional microbial subcommunities, or one or more defined microbial assemblages. Optionally, solubilized coal products can be treated with, for example, an antioxidant prior to addition of one or more microbes. One or more substantially pure or mixed populations of methanogens are included in at least one of said one or more microorganisms, one or more consortiums, one or more functional microbial subcommunities, or one or more defined microbial assemblages. In one embodiment, methane is produced by contacting at least one population of methanogens with the solubilized coal product. In another embodiment, $CO_2$ is produced by contacting at least one population of *Raoultella* spp., or species related thereto, with the solubilized coal product.

These and other objects and features of the invention will become more fully apparent when the following detailed description of the invention is read in conjunction with the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Unless defined otherwise, all technical and scientific terms used herein have the same meaning as commonly understood by one of ordinary skill in the art to which this invention is related. Many of the techniques and procedures described or referenced herein are well understood and commonly employed using conventional methodology by those skilled in the art. The following terms are defined for purposes of the invention as described herein.

The singular form "a", "an" and "the" include plural referents unless the context clearly dictates otherwise. Thus, for example, reference to "a cell" includes a plurality of cells and reference to "a compound" includes a plurality of compounds, etc.

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. All ranges provided within the application are inclusive of the values of the upper and lower ends of the range.

The term "substantially purified", as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

As used herein, the term "yield" refers to the amount of harvestable product, and is normally defined as the measurable produce of economical value of a product. Yield may be defined in terms of quantity and/or quality. The term "yield" also encompasses yield potential, which is the maximum obtainable yield. Yield may be dependent on a number of yield components, which may be monitored by certain parameters. These parameters are well known to persons in the art and vary.

As used herein, the terms "depolymerization", "solubilization" and "liquefaction" all refer to partial or complete breakdown of coal or lignocellulose biomass into one or more constituents (extracts).

Coal

Coal is a combination of mobile and stationary phases. Coal is a complex organic substance that is comprised of several groups of mackerels, or major organic matter types, which accumulate in different types of depositional settings such as peat swamps or marshes. Mercurial composition, and therefore coal composition, changes laterally and vertically within individual coal beds. The depolymerization, solubilization, and/or liquefaction of coal represent one step for the production of secondary biogenic coal bed methane. Coal depolymerization and solubilization technologies can therefore be used to transform a fraction of the solid coal matrix into soluble constituents that are more readily bioavailable.

The term "coal" as used herein refers to any rank of coal ranging from lignite to anthracite. The members of the various ranks differ from each other in the relative amounts of moisture, volatile matter, and fixed carbon contained in the matrix. The lowest in carbon content, lignite or brown coal, is followed in ascending order by subbituminous coal or black lignite (a slightly higher grade than lignite), bituminous coal, semi-bituminous (a high-grade bituminous coal), semi-anthracite (a low-grade anthracite), and anthracite. Coals for use in the present methods can be of any rank; representative examples of coal include, but are not limited to, lignite, brown coal, subbituminous coal, bituminous coal, coking coals, anthracite, and combinations thereof.

Lignocellulose

Lignocellulose is the primary component of biomass and the most abundant biological material on earth; fuels derived from lignocellulosic biomass are, thus, renewable energy alternatives that have the potential to sustain the economy, energy, and the environment worldwide.

As used herein, the term "lignocellulosic biomass" refers to plant biomass that is composed of cellulose, hemicellulose, and lignin. The carbohydrate polymers (cellulose and hemicellulases) are tightly bound to the lignin. Lignocellulosic biomass is can be grouped into four main categories: (1) agricultural residues (including, for example, corn stover and sugarcane bagasse), (2) dedicated energy crops, (3) wood residues (including sawmill and paper mill discards), and (4) municipal paper waste.

Cellulose, which is a β-glucan built up of anhydro D-glucose units, is the main structural component of plant cell walls and normally constitutes about 35-60% by weight (% w/w) of lignocellulosic materials.

Hemicellulose is a term used to denote non-cellulosic polysaccharides associated with cellulose in plant tissues. Hemicellulose frequently constitutes about 20-35% w/w of lignocellulosic materials, and the majority of hemicellulases consists predominantly of polymers based on pentose (five-carbon) sugar units, such as D-xylose and D-arabinose units, although more minor proportions of hexose (six-carbon) sugar units, such as D-glucose and D-mannose units, are generally also present.

Exemplary, non-limiting examples of lignocellulosic material include woody or herbaceous materials, agricultural or forestry residues, and dedicated energy crops. Materials include, but are not limited to, Salix, Poplar, Eucalyptus, grass (e.g., switch grass), *miscanthus*, sugar cane bagasse, stover (e.g., soybean stover, corn stover, etc.), rice straw, barley straw, wheat straw, corn fiber, cobs, stalks, husks, wood fiber, wood chips, wood shavings, wood residues, barks, bran, seeds, peels, fruit stones, shells, bagasse, leaves, saw dust, fiber waste, newspapers, office paper, cardboard, and combinations thereof.

Crops that can be harvested multiple times each year and which can provide high yields of biomass include, for example, popular trees, *Miscanthus giganteus* (a large perennial grass hybrid of *Miscanthus sinensis* and *Miscanthus sacchariflorus* useful as a source of heat and electricity, or converted into biofuel products such as ethanol), and sugarcane (a source of the readily fermentable sucrose and the lignocellulosic side product bagasse).

Lignocellulosic biomass represents a feedstock for the pulp and paper industry. Current industry methods focus on the separation of the lignin and cellulosic fractions of the biomass and are energy-intensive. The present application provides more energy-efficient and cost effective methods to solubilize lignocellulosic biomass for the pulp and paper industry.

Lignocellulosic biomass, in the form of wood, represents a precursor to liquid fuels such as, for example, ethanol, butanol, dimethylfuran, and gamma-Valerolactone. For example, the fermentation of lignocellulosic biomass to ethanol provides an alternative route to fuels that supplements the fossil fuels. Since biomass is a carbon-neutral source of energy because it originates from plants, the combustion of lignocellulosic ethanol produces no net carbon dioxide in the earth's atmosphere.

Lignocellulosic biomass also represents a low-cost source of mixed sugars for fermentation to fuel ethanol. Lignocellulose has a rigid structure and, in some instances, an effective treatment may be needed to liberate the cellulose from the lignin sheath and its crystalline structure to render it accessible for subsequent degradation. Lignocellulosic material can be treated to disrupt the fiber structure. Treatments include chemical means; chemical treatment can remove chemical barriers so that enzymes can access to cellulose for microbial degradation.

Lignocellulosic material can be treated in order to separate and/or release cellulose, hemicellulose, and lignin, thereby improving the rate of enzyme hydrolysis and further to increase fermentation product yields. The lignocellulosic material may during treatment be present in an amount between 10-80 wt. %, or between 20-50 wt.-%. The goal is to break down the lignin seal and disrupt the crystalline structure of the lignocellulosic material. The structure of the lignocellulosic material is altered and especially polymeric constituents are made more accessible to enzyme hydrolysis in later process steps where carbohydrate polymers (i.e., cellulose and hemicellulose) are converted into fermentable hexose and pentose sugars. Treatment can be carried out in any suitable way to separate and/or release cellulose, hemicellulose and/or lignin.

Lignocellulosic material to be treated using the present methods includes, but is not limited to: saw dust, wood pulp, paper pulp, paper pulp waste streams, grasses, such as, switchgrass, biomass plants and crops, such as, crambe, rice hulls, bagasse, jute, leaves, grass clippings, corn stover, corn cobs, corn grain, corn grind, distillers grains, and pectin.

Optionally, biomass to be treated can be fed into a chipper, grinder, chopper, shredder or the like, to be reduced in size. Biomass chips or particles can be about one-half inch or smaller.

Pyrophosphates

Salt and esters containing two phosphate groups are called diphosphates. The anion, the salts, and the esters of pyrophosphoric acid are diphosphates, which are known as pyrophosphates, which are chelators. The anion $P_2O_7^{4-}$ is abbreviated $PP_i$. The term "pyrophosphate" also refers to esters formed by the condensation of a phosphorylated biological compound with inorganic phosphate as for dimethylallyl pyrophosphate.

Non-limiting examples of pyrophosphates include, but are not limited to: sodium pyrophosphate ($NaP_2O_7$), calcium pyrophosphate ($Ca_2P_2O_7$), potassium pyrophosphate ($K_4P_2O_7$), ferrous pyrophosphate, ferric pyrophosphate, pyrophosphoric acid, or derivatives thereof. Derivatives include, for example, hexametaphosphate, sodium hexametaphosphate ($NaPO_3)_6$, sodium tripolyphosphate, and dibasic (e.g., disodium pyrophosphate; dicalcium pyrophosphate, dipotassium pyrophosphate, etc.) and tetrabasic (e.g., tetrasodium pyrophosphate—$Na_4P_2O_7$); tetracalcium pyrophosphate; tetrapotassium pyrophosphate, etc.) salts of cations, mainly sodium, calcium, potassium and iron.

Compositions comprising a pyrophosphate or a derivative thereof can be optimized based on the material to be treated. Factors, such as concentrations, temperature of the reaction conditions, pressure, pH and/or the time of treatment can also be taken into consideration when forming the composition.

Oxidants

Compositions for use in the methods described herein can further contain one or more oxidants. Oxidants include, but are not limited to, hypochlorites, permanganate, peroxides and the like.

Hypochlorites

Hypochlorites are the salts of hypochlorous acid. Due to their low stability and oxidation states, hypochlorites are very strong oxidizing agents. They react with many organic and inorganic compounds; reaction with organic compounds is very exothermic and can cause ignition. Hypochlorites can oxidize manganese compounds, converting them to permanganates.

Permanganate

Permanganate is the general name for a chemical compound containing the manganate(VII) ion ($MnO_4^-$); the manganate(VII) ion is a strong oxidizing agent because manganese is in the +7 oxidation state.

In an acidic solution, manganate(VII) is reduced to the colorless +2 oxidation state of the manganese(II) ($Mn^{2+}$) ion. In a strongly basic solution, manganate(VII) is either reduced to the brown +4 oxidation state of manganese dioxide $MnO_2$ or to the green +6 oxidation state of the manganate $MnO_4^{2-}$.

Permanganates can be produced by oxidation of manganese compounds by strong oxidizing agents, for instance, sodium hypochlorite or lead dioxide.

Peroxides

Organic peroxides are compounds with a specific functional group or a molecule containing an oxygen-oxygen single bond (R—O—O—R'). Peroxides useful in compositions for the methods described herein include, but are not limited to: hydrogen peroxide, carbamide peroxide, calcium peroxide, magnesium peroxide and the like.

Depolymerization, Solubilization Liquefaction

The methods of the present invention are capable of solubilizing coal and/or lignocellulose biomass. Suitable agents for solubilization include, for example, pyrophosphates, polymers of phosphate, or derivatives thereof.

Pyrophosphates to be contacted with coal or lignocellulose biomass include, but are not limited to, sodium pyrophosphate ($NaP_2O_7$), calcium pyrophosphate ($Ca_2P_2O_7$), potassium pyrophosphate ($K_4P_2O_7$), ferrous pyrophosphate, ferric pyrophosphate, pyrophosphoric acid, or a derivative thereof. Derivatives include, but are not limited to, hexametaphosphate, sodium tripolyphosphate, disodium pyrophosphate; dicalcium pyrophosphate, dipotassium pyrophosphate, tetrasodium pyrophosphate, tetracalcium pyrophosphate or tetrapotassium pyrophosphate.

In one aspect, the methods described herein comprise contacting coal or lignocellulose biomass with a composition comprising a pyrophosphate or a derivative thereof.

In another aspect, the compositions described herein can further contain one or more oxidants.

In one example, a composition utilized in the present methods comprises (i) a pyrophosphate, or a derivative thereof, and (ii) hypochlorite.

In another example, a composition utilized in the present methods comprises (i) a pyrophosphate, or a derivative thereof, and (ii) permanganate.

In yet another example, a composition utilized in the present methods comprises (i) a pyrophosphate, or a derivative thereof, (ii) hypochlorite and (iii) permanganate.

In certain embodiments, one or more peroxides can be further added to the treatment regimen.

Concentrations of treatment compounds, temperature, pressure pH and/or modes of administration of treatment compounds can be empirically determined depending upon the material to be treated.

As used herein, "depolymerization", "solubilization" and "liquefaction" are used interchangeably and collectively refer to mechanisms by which a solid coal matrix or lignocellulose biomass is transformed from a solid material into soluble constituents.

Coal

The present application describes use of coal solubilization technologies. Provided herein is a process for solubilization, depolymerization or liquefaction of coal into solubilized coal products, comprising: contacting coal with a composition comprising a pyrophosphate, or a derivative thereof, so as to cause solubilization or liquefaction of said coal. The method includes treating coal with a mixture of water and pyrophosphate under conditions effective to solubilize the coal. Optionally, a composition can be buffered with a phosphate buffer.

Also provided herein is a composition, comprising solubilized derivatives of coal produced by the methods described herein.

One advantage of the present invention is that the coal is solubilized with compounds such that the resulting solubilized derivatives can be further used for biogenic methane production.

Coal to be treated with the present methods can be of any rank of coal such as, for example, lignite, sub-bituminous coal, bituminous coal, or anthracite. In one embodiment, the process occurs in situ (i.e., in a subterranean coal deposit). In another embodiment, the process occurs ex situ. Coal can be pretreated (e.g., by grinding ex situ, fracturing in situ, etc.) so as to render the coal uniformly and more readily susceptible to solubilization. Deep coal mines can have temperatures near the boiling point of water; the compositions described herein are compatible with such temperatures.

Treatment can be carried out at a temperature of ambient temperature to about 500° C. In one embodiment, the temperature of the reaction is conducted at ambient temperature. The temperature of the reaction can conducted at a temperature of from about 25° C. to about 500° C., from about 50° C. to about 250° C., from about 100° C. to about 200° C., from about 200° C. to about 300° C., from about 300° C. to about 400° C., from about 75° C. to about 175° C., or about 90° C. to about 120° C. In one embodiment, an aqueous treatment composition having a temperature of ambient temperature, at or about 20° C., at or about 50° C., at or about 100° C., at or about 120° C., at or about 150° C., at or about 175° C., at or about 200° C. or at or about 250° C. is contacted with a coal sample.

A composition comprising a pyrophosphate or a derivative thereof contains a sufficient amount of the pyrophosphate or a derivative thereof to solubilize coal. For example, in an ex situ reactor, a concentration of pyrophosphate in the vessel can be maintained at about 0.05%, about 0.1%, about 0.2%, about 0.5%, about 1%, about 2.5%, about 5%, about 7.5%, about 10%, about 20%, about 30% or about 40%, of the mass of coal. The concentration of pyrophosphate added to a reactor or an in situ coal deposit (formation) can be up to about 500 mM. Exemplary ranges of pyrophosphate to be added in solution to a coal sample can be between about 0.05 mM and about 500 mM; between about 1 mM and 500 mM; between about 50 mM and about 250 mM; between about 50 mM and about 100 mM; between about 75 mM and about 150 mM, between about 1 mM and about 50 mM; between about 5 mM and about 25 mM; between about 10 mM and about 20 mM; between about 100 mM and about 200 mM, between about 200 mM and about 300 mM, between about 300 mM and about 400 mM; or between about 150 mM and about 250 mM. In one embodiment, pyrophosphate is contacted with coal at a final concentration of 100 mM. Acceptable excipients for such compositions include, but are not limited to, water or water buffered with a phosphate solution at, or below, pH 9. One advantage of the present methods is that pyrophosphate is able to solubilize coal and release organic carbon when added in millimolar concentrations. Thus, a lower amount of the chemical is needed compared to other solubilization chemicals.

Treatment can be carried out at any pH; pH can be empirically determined and changed to obtain optimal treatment conditions. In one embodiment, the pH of a composition comprising a pyrophosphate or derivative thereof is above neutral pH. For example, the pH can be in the range of about pH 2-11, about pH 8-10, about 2, about 7 or about pH 9.

Pressure in an ex situ reactor vessel can be in a range of from atmospheric pressure to about 100 psi; for example, pressure can be atmospheric pressure, at or about 50 psi, at or about 75 psi, at or about 100 psi, at or about 250 psi, at or about 300 psi, at or about 500 psi, at or about 750 psi or at or about 1000 psi or any integer therebetween. Alternatively, wherein treatment is of an in situ coal formation, pressure can be that of the in situ environment.

The residence time of a coal sample to be treated in the reactor can be from about 3 seconds to about 4 weeks. Treatment time can be optimized, for example, depending upon the rank of coal to be treated, the total mass to be treated, and in situ or ex situ parameters. Treatment time can be for about 30 seconds, 1 minute, 2 minutes, 5 minutes, 10 minutes, about 20 minutes, about 30 minutes, about 40 minutes, about 50 minutes, about 60 minutes, about 2 hours, about 5 hours, about 10 hours, about 24 hours, about 48 hours, about 72 hours, about 1 week, about 2 weeks, about 3 weeks or about 4 weeks.

Coal to liquid ratios can be optimized based on the coal to be treated and whether the reaction takes place in an ex situ reactor or an in situ coal deposit. Coal to liquid (composition) ratios include, for example 4% to 30% coal to liquid (weight by volume).

Using the methods described herein, coal can be sufficiently solubilized (partially or completely. The methods can transform a fraction of the solid coal matrix into soluble constituents. In certain instances, at least about 5% of a solid coal matrix is solubilized. In other instances, at least about 10%, 20%, 30%, 40%, 50%, 60%, 70%, 75%, 80%, 85%, 90%, 95%, 100%, or any integer inbetween of a solid coal mass is solubilized.

In some embodiments, solubilization increases the available dissolved organic carbon as identified by high to low molecular weight shifts.

Solubilized end products can be further used to facilitate biogenic methane production. Optionally, solubilized coal products can be treated with one or more antioxidant reagents prior to initiating microbial enhanced methane production. Such reagents act as electron scavengers and include, but are not limited to, sulfite, sodium sulfite, sodium bisulfate, and ascorbate.

In one embodiment, the methods further comprise contacting the solubilized coal with one or more nutrients, one or more additives, one or more stimulants, one or more microorganisms (e.g., methanogens), one or more microbial consortiums, one or more functional microbial subcommunities, one or more defined microbial assemblages or a combination thereof to facilitate biogenic methane production. Microorganisms can be indigenous or exogenous to the formation to be treated. Microorganisms can be naturally-occurring or genetically engineered. Where more than one population of microorganisms is to be introduced, one or more populations can be genetically engineered and one or more populations can be genetically unmodified. A "methanogen" as used herein, refers to obligate and facultative anaerobic microorganisms that produce methane from a metabolic process. Optionally, the coal may require further treatment or conditioning after solubilization and before exposure to microbial conversion to methane.

The term "defined microbial assemblage" or "DMA" as used herein, refers to a culture of more than one microorganism, wherein different strains are cultured or intentionally combined to convert a hydrocarbon to methane. The microorganisms of the assemblage are "defined" such that at any point in time, the members of the population can be determined by use of genetic methods, such as 16S taxonomy as described herein. A DMA does not necessarily remain static over time, but may evolve as cultures flux to optimize hydrocarbon hydrolysis and methane production. Optimally, the DMA is prepared to provide microorganisms harboring strong capacity to convert hydrocarbon to methane. The DMA may consist of 2 or more microorganisms, in any combination, to provide bacterial or archael species capable of converting a hydrocarbon to any intermediate leading to the production of methane, and/or any methanogenic species. For example, there may be 2, 3, 4, 5, 6, 7, 8, 9, 10, 11, 12, 13, 14, 15 or more organisms present in a DMA. The members of the DMA act synergistically to produce methane, amongst themselves, or together with microorganisms present in the hydrocarbon-bearing formation.

The term "microorganism" is intended to include bacterial and archaeal organisms, as well as fungi, yeasts and molds. It will be understood that bacteria and archaea are representative of microorganisms in general that can convert the resulting products to methane. The dividing lines between classes of microorganisms are not always distinct. It is preferred, therefore, to use the term microorganisms to include all microorganisms that can convert hydrocarbons to methane, whatever the commonly used classifications might be. Of these microorganisms, those usually classified as bacteria and archaea such as, for example, acetogens and methanogens are preferred. If exogenous bacteria and archaea are used in the methods described herein, other microorganisms such as fungi, yeasts, molds, and the like can also be used.

The term "anaerobic microorganism" as used herein, refers to microorganisms that can live and grow in an atmosphere having less free oxygen than troposphere air (i.e., less than about 18%, by mol., of free oxygen). Anaerobic microorganisms include organisms that can function in atmospheres where the free oxygen concentration is less than about 10% by mol., or less than about 5% by mol., or less than about 2% by mol., or less than about 0.5% by mol.

The term "facultative anaerobes" as used herein, refers to microorganisms that can metabolize or grow in environments with either high or low concentrations of free oxygen.

Microorganisms described herein also include those that can grow in the presence of solubilized coal extracts and/or convert solubilized coal extracts to $CO_2$. Examples of such microorganisms include, but are not limited to *Raoultella* spp. or species related thereto.

All methanogenic microorganisms are believed to employ elements of the same biochemistry to synthesize methane. Classes of methanogens include *Methanobacteriales, Methanomicrobacteria, Methanopyrales, Methanococcales*, and *Methanosaeta* (e.g., *Methanosaeta thermophila*), among others. Specific examples of methanogens include *Methanobacter thermoautotorophicus*, and *Methanobacter wolfeii*. Methanogens may also produce methane through metabolic conversion of alcohols (e.g., methanol), amines (e.g., methylamines), thiols (e.g., methanethiol), and/or sulfides (e.g., dimethyl sulfide). Examples of these methanogens include methanogens from the genera *Methanosarcina* (e.g., *Methanosarcina barkeri, Methanosarcina thermophila, Methanosarcina siciliae, Methanosarcina acidovorans, Methanosarcina mazeii, Methanosarcinafrisius*); *Methanolobus* (e.g., *Methanolobus bombavensis, Methanolobus tindarius, Methanolobus vulcani, Methanolobus taylorii, Methanolobus oregonensis*); *Methanohalophilus* (e.g., *Methanohalophilus mahii, Methanohalophilus euhalobius*); *Methanococcoides* (e.g., *Methanococcoides methylutens, Methanococcoides burtonii*); and/or *Methanosalsus* (e.g., *Methanosalsus zhilinaeae*). They may also be methanogens from the genus *Methanosphaera* (e.g., *Methanosphaera stadtmanae* and *Methanosphaera cuniculi*, which are shown to metabolize methanol to methane). They may further be methanogens from the genus *Methanomethylovorans* (e.g., *Methanomethylovorans hollandica*, which is shown to metabolize methanol, dimethyl sulfide, methanethiol, monomethylamine, dimethylamine, and trimethylamine into methane).

Stimulants and nutrients include, for example, yeast extract, sulfur, an oxyanion of sulfur (e.g., thiosulfate ($S_2O_3$), sodium thiosulfate ($Na_2S_2O_3$), potassium thiosulfate ($K_2S_2O_3$), sulfuric acid, disulfuric acid, peroxymonosulfuric acid, peroxydisulfuric acid, dithionic acid, thiosulfuric acid, disulfurous acid, sulfurous acid, dithionus acid or polythionic acid), $NH_4Cl$, KCl, vanadium, $VCl_3$, $VCl_2$, VCl, $Na_2SO_3$, $MnCl_2$, $Na_2MoO_4$, $FeCl_3$ or $Na_2SO_4$, potassium phosphate, sodium acetate, etc.

Lignocellulose Biomass

Using the methods described herein, lignocellulosic material (biomass) can be sufficiently solubilized. In some instances, the solubilized end products can be further used to create a product (e.g., ethanol). Lignocellulose biomass can be fed into a chipper, grinder, chopper, shredder or the like to be reduced in size prior to exposure to said pyrophosphate, for example, to increase the surface are of the biomass material to be treated and/or decrease time required for solubilization.

Provided herein is a process for solubilization, depolymerization or liquefaction of lignocellulose biomass into solubilized products, comprising: exposing lignocellulose biomass to a composition comprising a pyrophosphate so as to cause solubilization or liquefaction of said lignocellulosic material.

Lignocellulose biomass to be treated includes, but is not limited to: saw dust, wood flour, wood pulp, paper pulp, paper pulp waste streams, one or more grasses (e.g., switchgrass), crambe, rice hulls, bagasse, jute, leaves, grass clippings, corn stover, corn cobs, corn grain, corn grind, distillers' grains, or pectin.

Solubilization of lignocellulose biomass can occur in a reactor.

Sufficient pyrophosphate can be added to the reactor to maintain a concentration of pyrophosphate in the vessel of 0.05%, 0.1%, 0.2%, 0.5%, 1%, 2.5%, 5%, 7.5%, 10%, or 20% of the lignocellulose. The concentration of pyrophosphate added to the reactor can be between about 0.5 µM and about 1 M; between about 1 µM and 500 µM; between about 50 µM and about 250 µM; between about 50 µM and about 100 µM; between about 1 µM and about 50 µM; between about 5 µM and about 25 µM; or between about 10 µM and about 20 µM.

Treatment can be carried out at a temperature of ambient temperature to about 200° C.; at ambient temperature to about 150° C.; from about 50° C. to about 150° C.; or from about 80° C. to about 100° C.

Treatment can be carried out at any pH; pH can be empirically determined and changed to obtain optimal treatment conditions. In one embodiment, the pH can be in the range of about 6 to about 13; about 6 to about 9; about 9 to about 12, from about 7 to about 10, or about 7.

Pressure in a reactor vessel can be atmospheric pressure to 100 psi; for example, pressure can be atmospheric pressure, 50 psi, 75 psi, 100 psi, 250 psi, 300 psi, 500 psi, 750 psi or 100 psi or any integer therebetween.

In one embodiment, an aqueous treatment composition having a temperature of ambient temperature, 20° C., 50° C., 100° C., 120° C., 150° C., 175° C., 200° C. or 250° C. is fed into a reactor vessel at the other end at a rate of 5,000 kilograms per hour.

The residence time of the biomass to be treated in the reactor can be from about 10 minutes to about 30 days. Treatment time can be optimized, for example, depending upon the density of the biomass to be treated, the total volume to be treated, and any other considerations. Treatment time can be for about 10 minutes, about 20 minutes, about 30 minutes, about 40 minutes, about 50 minutes, about 60 minutes, about 2 hours, about 5 hours, about 10 hours, about 24 hours, about 48 hours, about 72 hours, about 1 week, about 2 weeks, about 3 weeks or about 4 weeks.

The discussion of the general methods given herein is intended for illustrative purposes only. Other alternative methods and embodiments will be apparent to those of skill in the art upon review of this disclosure. The following examples are offered to illustrate, but not limit, the invention.

EXAMPLES

Example 1

Solubilization of Coal with Sodium Salts of Pyrophosphate and Hexametaphosphate The ability of tetrasodium pyrophosphate and sodium hexametaphosphate to solubilize coal (lignite and/or subbituminous) and/or release organic carbon from a coal sample were assessed.

(1) Tetrasodium Pyrophosphate (a) Stock Solutions

A primary stock of 600 mM sodium phosphate buffer at pH 7 was made by adding 82.8 g monobasic sodium phosphate monohydrate (Fisher) to 1000 ml of 18 MΩ water and the pH was adjusted to 7 with 5 N sodium hydroxide; another 1000 ml aliquot of 600 mM sodium phosphate buffer at pH 2 was made by adding 41 ml of 85% orthophosphoric acid solution to 959 ml of 18 MΩ water and adjusting the ph to 2 with 5 N sodium hydroxide. Working solutions of 200 mM tetrasodium pyrophosphate in 600 mM sodium phosphate buffer solutions were made by combining 150 ml of the buffer with 13.4 g tetrasodium pyrophosphate and adjusting the pH (if needed) to either 7 or 2 with concentrated hydrochloric acid or 5 N NaOH. A potassium permanganate working stock solution was made by combining 11.85 g potassium permanganate (Sigma) with 250 ml 18 MΩ water for a final concentration of 300 mM. Hypochlorite (Fisher, Cat. No. SS290-1) is added neat for a final concentration of 100 mM.

(b) Coal

Ground samples of lignite (North American Coal Co.) and sub-bituminous coal (BHP Billiton) were sieved through a 250 µm sieve onto a 150 µm sieve. Using 18 MΩ water, this fraction was washed extensively on the 150 µm sieve to remove finer particles. Separate sieves were used for each coal type. The coal was oven dried at 80° C. overnight and distributed in 0.5 g aliquots into acid-washed glass tubes.

(c) Treatments

All treatments were comprised of 12 ml liquid added to 0.5 g coal. Stock solutions, 18 MΩ water and neat hypochlorite (800 mM) were combined in glass tubes in the appropriate volumes to create 24 treatment compositions for each coal; duplicate tubes were made for each condition.

| Condition | Tetrasodium pyrophosphate (mM) | Sodium phosphate (mM) | Permanganate (mM) | Hypochlorite (mM) | pH (mM) |
|---|---|---|---|---|---|
| 1 | 0 | 300 | 0 | 0 | 2 |
| 2 | 0 | 300 | 0 | 100 | 2 |
| 3 | 0 | 300 | 100 | 0 | 2 |
| 4 | 0 | 300 | 100 | 100 | 2 |
| 5 | 100 | 300 | 0 | 0 | 2 |
| 6 | 100 | 300 | 0 | 100 | 2 |
| 7 | 100 | 300 | 100 | 0 | 2 |
| 8 | 100 | 300 | 100 | 100 | 2 |
| 9 | 0 | 300 | 0 | 0 | 7 |
| 10 | 0 | 300 | 0 | 100 | 7 |
| 11 | 0 | 300 | 100 | 0 | 7 |
| 12 | 0 | 300 | 100 | 100 | 7 |
| 13 | 100 | 300 | 0 | 0 | 7 |
| 14 | 100 | 300 | 0 | 100 | 7 |
| 15 | 100 | 300 | 100 | 0 | 7 |
| 16 | 100 | 300 | 100 | 100 | 7 |
| 17 | 0 | 0 | 0 | 0 | uc* |
| 18 | 0 | 300 | 0 | 100 | uc* |
| 19 | 0 | 300 | 100 | 0 | uc* |
| 20 | 0 | 300 | 100 | 100 | uc* |
| 21 | 100 | 300 | 0 | 0 | 9 |
| 22 | 100 | 300 | 0 | 100 | 9 |
| 23 | 100 | 300 | 100 | 0 | 9 |
| 24 | 100 | 0 | 100 | 100 | 9 |

*uc = uncontrolled

After all solutions were combined in each glass tube, the contents of each tube was poured into a tube containing coal and this tube was closed with a butyl rubber stopper, crimp-sealed with aluminum caps and incubated for 24 hours in a 50° C. water bath without shaking. Incubations were terminated by centrifuging the contents of each tube and filtering the supernatant through a Whatman GF/F glass fiber filter.

(d) Assays

Soluble total organic carbon (sTOC) in each filtered supernatant was determined on a Shimadzu TOC-V Total Organic Carbon Analyzer (Shimadzu Scientific Instruments, Columbia, Md.) by subtracting carbon dioxide evolved by acid treatment of each sample (inorganic carbon) from that detected after combustion of a specific volume on a palladium catalyst (total carbon). Total carbon and inorganic carbon values were taken as the best two of three injections values. Low, medium and high standard curves were made with the instrument auto-dilution protocol according to the manufacturer's instructions using 100, 1000 and 5000 ppm standards of potassium hydrogen phthalate (for total carbon) and sodium (bi)carbonate (inorganic carbon). Samples found to be outside of the low or medium curve were re-injected and re-measured using the next highest standard curve.

(e) Analyses

The sTOC concentration was converted from mg/l (ppm) to g/l and then to an absolute value (g) by multiplying by the total incubation volume of 0.012 l. To determine the fraction of coal organic carbon solubilized, the sTOC (in g) was divided by the mass of organic carbon added to each tube based on the percent organic carbon in each coal. The percent organic carbon was determined, by an outside vendor, to be 57% and 62% (dry weight basis) for the lignite and sub-bituminous coals, respectively. Water gained from atmospheric water vapor during the short period between removing the coal from the drying oven and weighing was disregarded as additional weight gained from moisture prior to weighing would decrease the total coal added to each tube and increase the fraction of coal organic carbon solubilized; thus, the reported numbers are conservative.

(2) Sodium Hexametaphosphate (SHMP)

An accelerated solvent extractor (ASE®) was used to solubilize 2.0 g of lignite coal (BCS-03). A 5.1% (w/v) solution of SHMP was made in deionized water. ASE® parameters (time, temperature and SHMP mixing ratio) were varied as indicated in the table below.

SHMP contains 6 phosphates, that is 3 times (3×) that of PPi, so the experiments was designed using ⅓ of the relative concentration of PPi. That is, 250 mM of PPi=83.3 mM of SHMP. The pH of 2 L solutions of SHMP in milliΩ water containing the concentrations of hexametaphosphate described below were adjusted from pH 6.86 to pH 7.

| Sample vessel no. | Time (minutes) | Temperature (° C.) | Concentration of PPi relative to hexametaphosphate (mM) | Concentration of hexametaphosphate (mM) |
|---|---|---|---|---|
| 1 | 75 | 75 | 150 | 50 |
| 2 | 120 | 75 | 50 | 16.7 |
| 3 | 120 | 75 | 250 | 83.3 |
| 4 | 30 | 75 | 250 | 83.3 |
| 5 | 30 | 75 | 50 | 16.7 |
| 6 | 30 | 138 | 150 | 50 |
| 7 | 75 | 138 | 150 | 50 |
| 8 | 75 | 138 | 150 | 50 |
| 9 | 120 | 138 | 150 | 50 |
| 10 | 75 | 138 | 50 | 16.7 |
| 11 | 75 | 138 | 150 | 50 |
| 12 | 75 | 138 | 250 | 83.3 |
| 13 | 30 | 200 | 250 | 83.3 |
| 14 | 120 | 200 | 250 | 83.3 |
| 15 | 30 | 200 | 50 | 16.7 |
| 16 | 75 | 200 | 150 | 50 |
| 17 | 120 | 200 | 50 | 16.7 |

Two (2) grams of lignite coal (BCS-3) was added into each of the reaction vessels.

Each sample was loaded onto an accelerated solvent extractor (ASE®) (Dionex, Corp., Dionex ASE350) and run overnight.

Control water samples were tested in a prior experiment and the amount of total organic carbon following exposure of lignite coal to water was determined to be 0.

Figure 5:
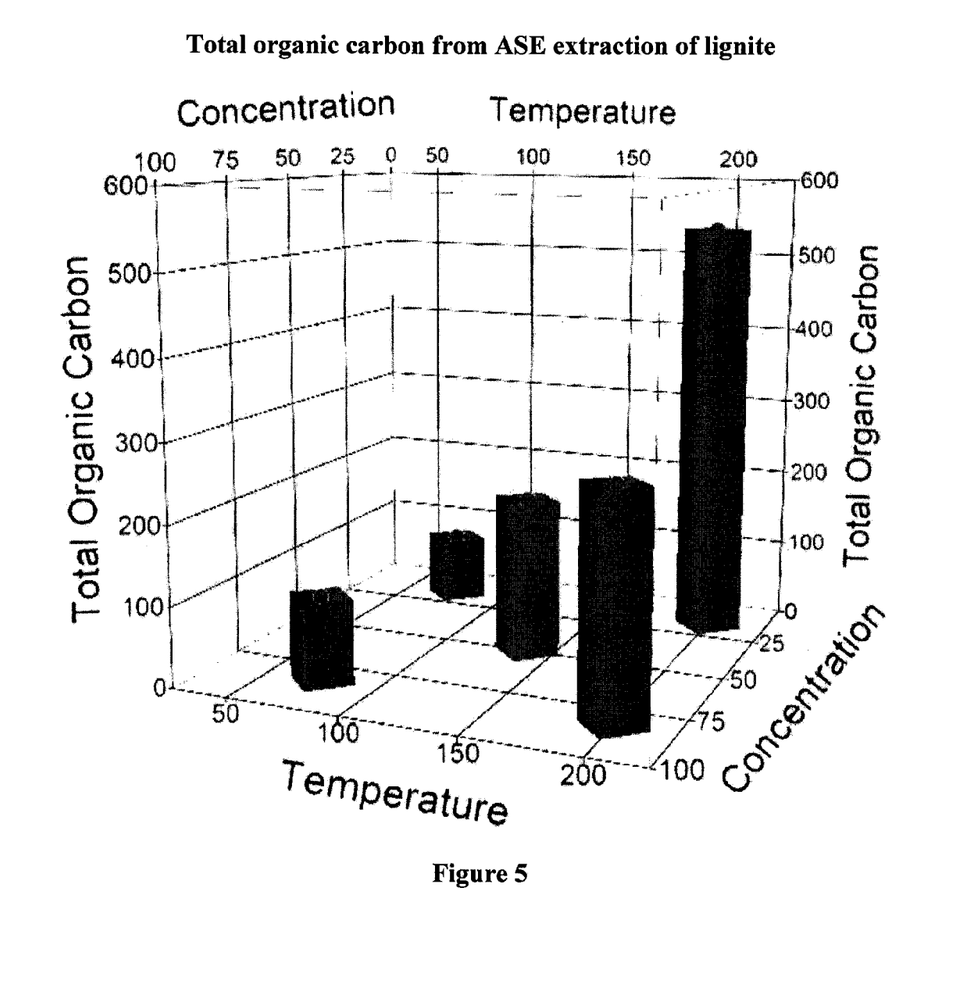
FIG. 5 illustrates TOC after an accelerated solvent extractor (ASE®) was used to solubilize lignite coal with sodium hexametaphosphate $(NaPO_3)_6$ for 2 hours.
Figure 6:
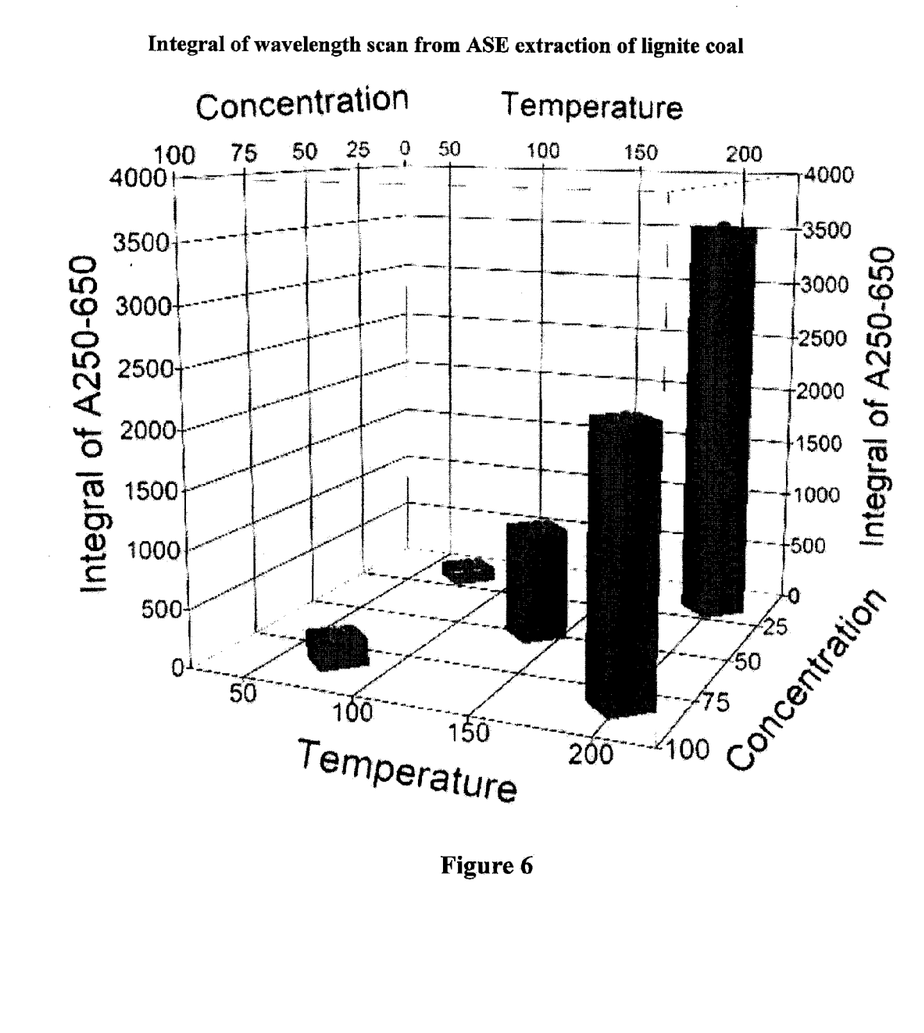
FIG. 6 provides a 3D scatter plot illustrating an integral of wavelength scan from ASE® extraction of lignite coal following solubilization of lignite coal with sodium hexametaphosphate $(NaPO_3)_6$.

Following treatment, solid and liquid samples were assayed for total organic carbon (FIG. 5) and subjected to an integral wavelength scan from $A_{250-650}$ (FIG. 6).

(3) Discussion

Organic carbon compounds from coal solids were solubilized by treating the solids with polymers of phosphate, such as sodium salts of pyrophosphate and hexametaphosphate. Both sub-bituminous and lignite coals were found to be partly solubilized by sodium pyrophosphate alone and in conjunction with oxidants (hypochlorite and/or permanganate).

Lignite and subbituminous coal were solubilized to different extents using compositions of pyrophosphates, permanganate, hypochlorite, a combination of pyrophosphates and hypochlorite, a combination of pyrophosphates and permanganates, a combination of hypochlorite and permanganate, or a combination of pyrophosphates, hypochlorite and permanganate.

Sodium pyrophosphate may solubilize coal directly by chelating cations that hold the macromolecular coal structure together and/or by maintaining an alkaline pH as a buffer.

Figure 1:
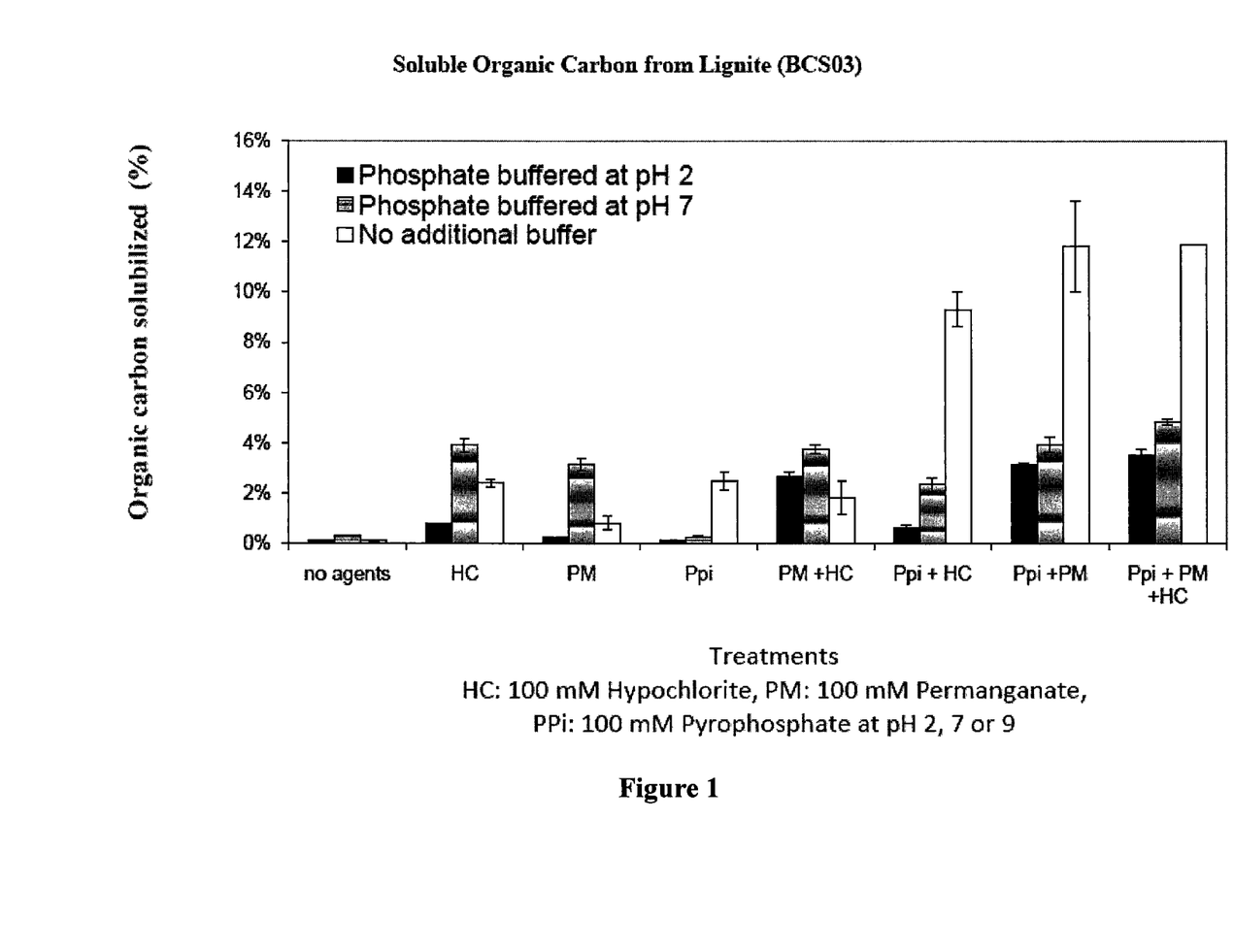
FIG. 1 illustrates the percentage of organic carbon solubilized with water (no agents), hypochlorite (HC) alone, permanganate (PM) alone, pyrophosphate (Ppi) alone, PM+HC, Ppi+PM, or Ppi+HC, Ppi+PM+HC.
Figure 2:
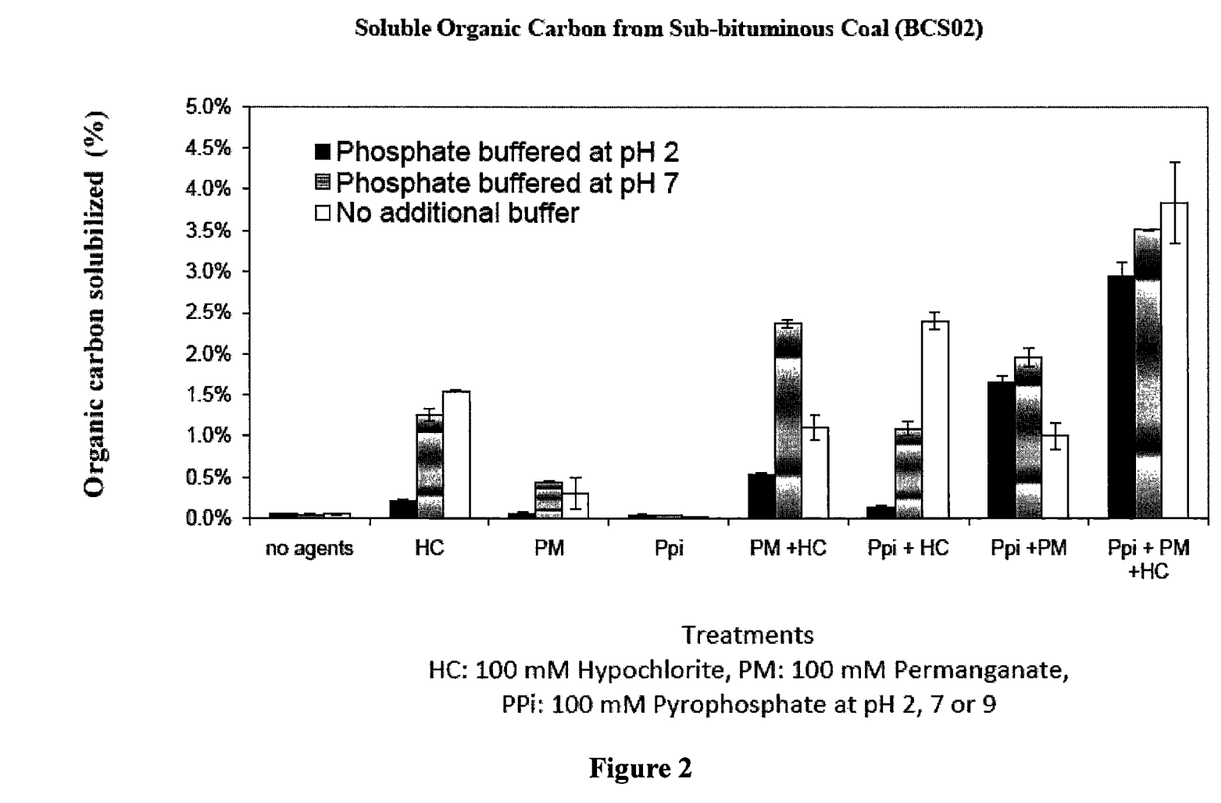
FIG. 2 illustrates the percentage of organic carbon solubilized with water (no agents), hypochlorite (HC) alone, permanganate (PM) alone, pyrophosphate (Ppi) alone, PM+HC, Ppi+PM, or Ppi+HC, Ppi+PM+HC.
Figure 3:
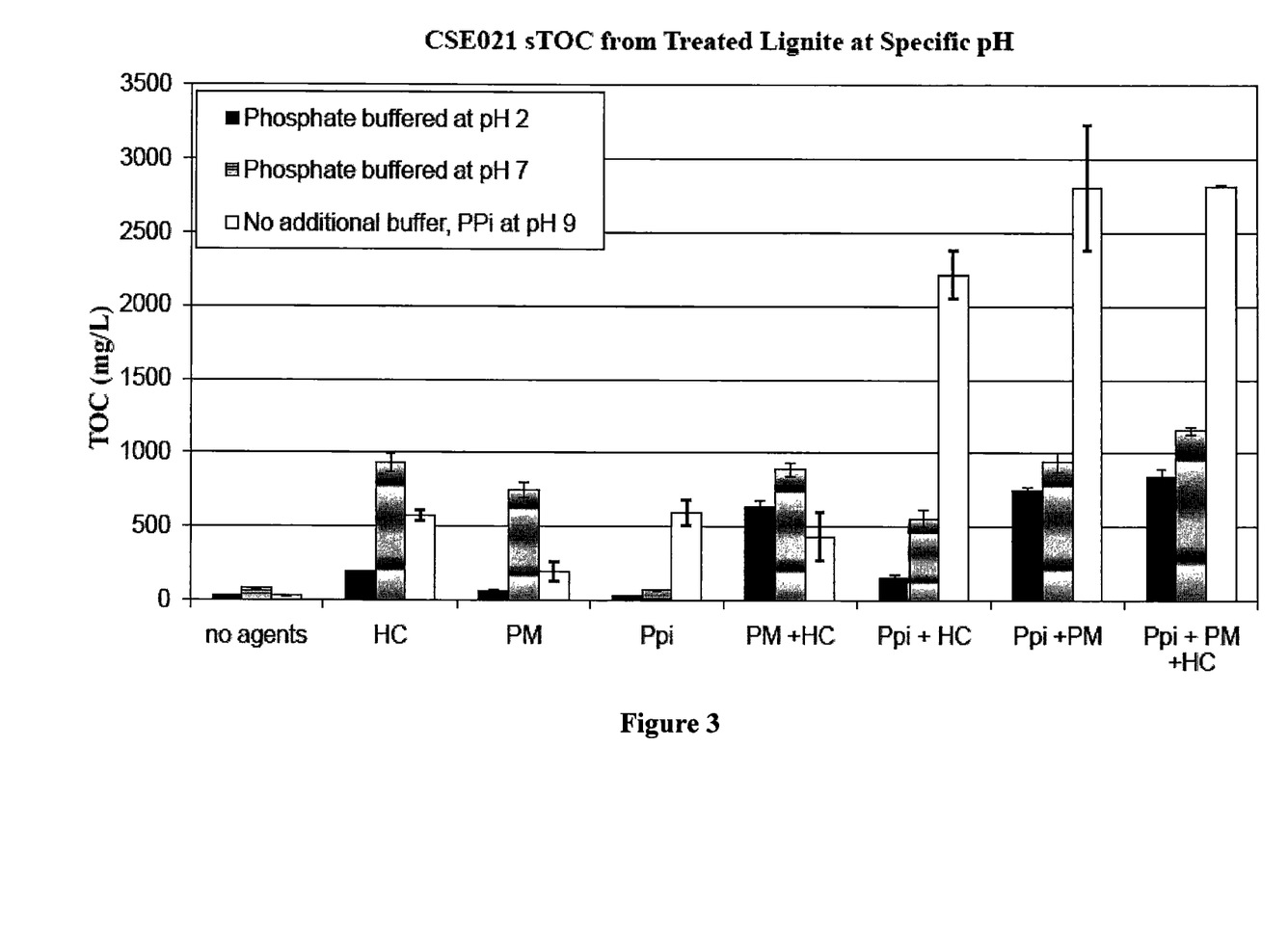
FIG. 3 illustrates total organic carbon (TOC; mg/L) observed from lignite treated with hypochlorite (HC) alone, water (no agents), permanganate (PM) alone, PM+HC, pyrophosphate (Ppi) alone, Ppi+HC, Ppi+PM+HC or Ppi+PM.
Figure 4:
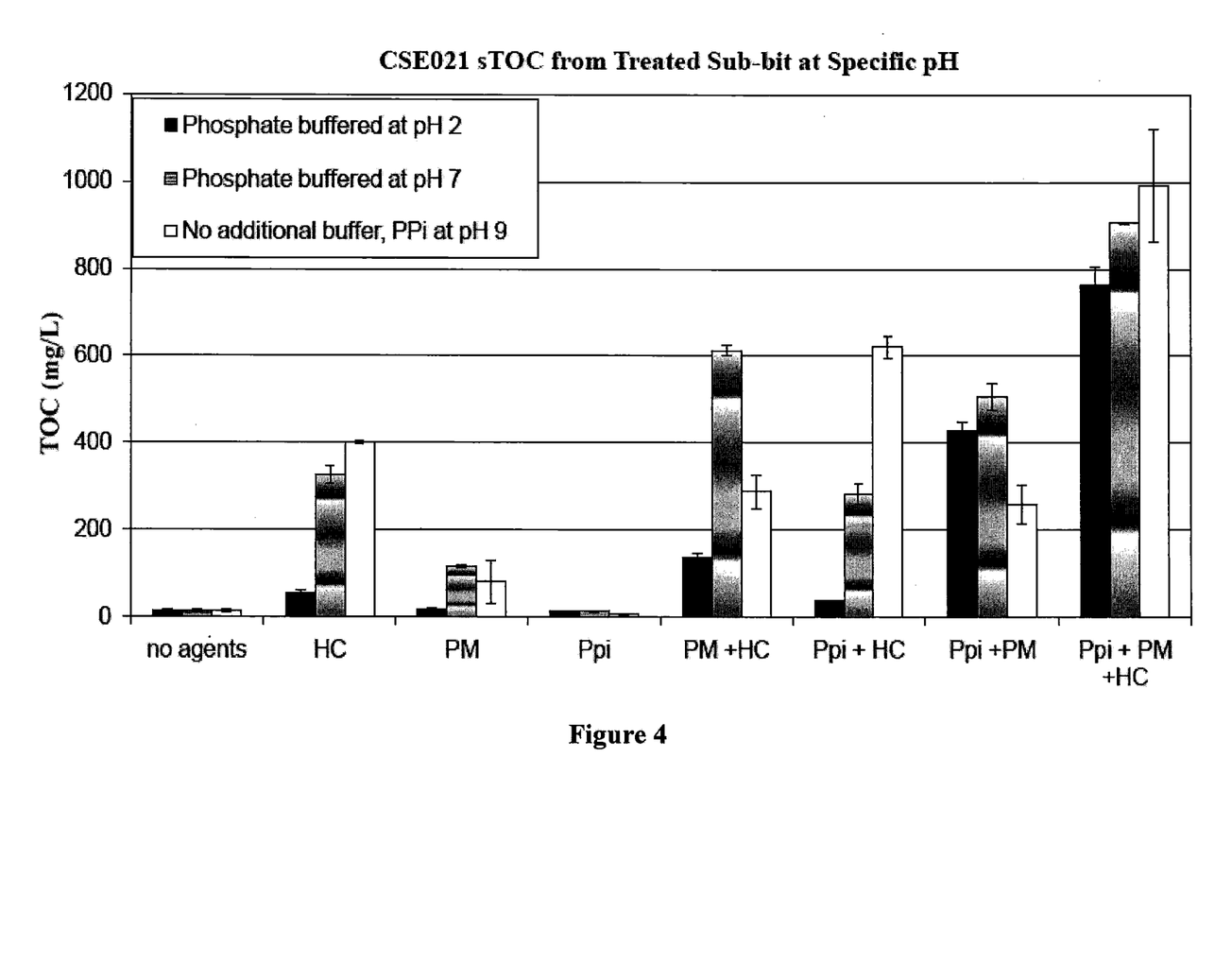
FIG. 4 illustrates TOC (mg/L) observed from subbituminous coal treated with hypochlorite (HC) alone, water (no agents), permanganate (PM) alone, PM+HC, pyrophosphate (Ppi) alone, Ppi+HC, Ppi+PM+HC or Ppi+PM.

The results indicate that sodium pyrophosphate unexpectedly acted in synergy with oxidants (hypochlorite and/or permanganate) upon coal, increasing the percentage of organic carbon solubilized (see FIGS. 1 and 2) and the total organic carbon released (see FIGS. 3 and 4).

Carbon dioxide was produced from lignite and subbituminous coal when exposed to Mn(III)-pyrophosphate. An increased colored material was released from lignite by pyrophosphate compared to phosphate; however, manganese was not determined to play a role in the reaction as solubilization was observed in the presence of pyrophosphate alone (data not shown). Increased absorbance at 450 nM and 255 nm from lignite treatment was observed following treatment with pyrophosphate alone indicating that the coal was being solubilized. Following treatment of subbituminous coal with pyrophosphate alone, an increase in absorbance was only observed at 255 nm (data not shown).

These results indicate that pyrophosphate alone is capable of solubilizing lignite coal; the addition of hypochlorite or permanganate to pyrophosphate in the treatment composition was found to be sufficient to partially solubilize subbituminous coal.

Synergistic effects for solubilizing lignite coal were observed for the combinations of (1) pyrophosphate and hypochlorite at pH 9; and (2) pyrophosphate and permanganate at pH 9. Addition of all three compounds increased total organic carbon at pH 9 compared to samples containing pyrophosphate and hypochlorite or pyrophosphate and permanganate (FIG. 3).

Synergistic effects for solubilizing subbituminous coal were observed for the combinations of (1) pyrophosphate and hypochlorite at pH 9; (2) pyrophosphate and permanganate at pH 2, pH 7 and pH 9; and (3) pyrophosphate, permanganate and hypochlorite at pH 2 and pH 7 compared to control samples. An additive effect was seen with the combination of permanganate and hypochlorite at pH 7 compared to control samples (FIG. 4).

Sodium hexametaphosphate is a chelator that has an acidic-neutral pH when dissolved in water. This delineates the pH effects of chelator solubilization (pyrophosphate at pH 9) from the chelation effects (SHMP or pyrophosphate at neutral pH).

Sodium hexametaphosphate (SHMP) acts in a manner similar to pyrophosphate and is able to extract ≥500 mg/L total organic carbon from lignite. Total organic carbon measured and an integral of wavelength scan are illustrated in FIGS. 5 and 6, respectively. Increasing the temperature increased solubilization. Extended incubation at higher temperatures decreased the effects of concentration on solubilization.

Example 2

Solubilization of Coal with Sodium Salts of Hexametaphosphate (a) Stock Solutions A primary stock of 600 mM sodium phosphate buffer at pH 7 is made by adding 82.8 g monobasic sodium phosphate monohydrate to 1000 ml of 18 MΩ water and the pH is adjusted to 7 with 5 N sodium hydroxide; another 1000 ml aliquot of 600 mM sodium phosphate buffer at pH 2 is made by adding 41 ml of 85% ortho-phosphoric acid solution to 959 ml of 18 MΩ water and adjusting the ph to 2 with 5 N sodium hydroxide. Working solutions of 66.7 mM sodium hexametaphosphate in 600 mM sodium phosphate buffer solutions are made by combining 150 ml of the buffer with 4.47 g sodium hexametaphosphate and adjusting the pH (if needed) to either 7 or 2 with concentrated hydrochloric acid or 5 N NaOH. A potassium permanganate working stock solution is made by combining 11.85 g with 250 ml 18 MΩ water for a final concentration of 300 mM. Hypochlorite (Fisher, Cat. No. SS290-1) is added neat for a final concentration of 100 mM.

(b) Coal

Ground samples of North American lignite and sub-bituminous coal are sieved through a 250 μm sieve onto a 150 μm sieve. Using 18 MΩ water, this fraction is washed extensively on the 150 μM sieve to remove finer particles. Separate sieves are used for each coal type. The coal is oven dried at 80° C. overnight and distributed in 0.5 g aliquots into acid-washed glass tubes.

(c) Treatments

All treatments are comprised of 12 ml liquid added to 0.5 g coal. Stock solutions, 18 MΩ water and neat hypochlorite (800 mM) are combined in glass tubes in the appropriate volumes to create 24 treatment compositions for each coal; duplicate tubes are made for each condition.

| Condition | Sodium hexametaphosphate (mM) | Sodium phosphate (mM) | Permanganate (mM) | Hypochlorite (mM) | pH (mM) |
|---|---|---|---|---|---|
| 1 | 0 | 300 | 0 | 0 | 2 |
| 2 | 0 | 300 | 0 | 100 | 2 |
| 3 | 0 | 300 | 100 | 0 | 2 |
| 4 | 0 | 300 | 100 | 100 | 2 |
| 5 | 33.3 | 300 | 0 | 0 | 2 |
| 6 | 33.3 | 300 | 0 | 100 | 2 |
| 7 | 33.3 | 300 | 100 | 0 | 2 |
| 8 | 33.3 | 300 | 100 | 100 | 2 |
| 9 | 0 | 300 | 0 | 0 | 7 |
| 10 | 0 | 300 | 0 | 100 | 7 |
| 11 | 0 | 300 | 100 | 0 | 7 |
| 12 | 0 | 300 | 100 | 100 | 7 |
| 13 | 33.3 | 300 | 0 | 0 | 7 |
| 14 | 33.3 | 300 | 0 | 100 | 7 |
| 15 | 33.3 | 300 | 100 | 0 | 7 |
| 16 | 33.3 | 300 | 100 | 100 | 7 |
| 17 | 0 | 0 | 0 | 0 | uc* |
| 18 | 0 | 300 | 0 | 100 | uc* |
| 19 | 0 | 300 | 100 | 0 | uc* |
| 20 | 0 | 300 | 100 | 100 | uc* |
| 21 | 33.3 | 300 | 0 | 0 | 9 |
| 22 | 33.3 | 300 | 0 | 100 | 9 |
| 23 | 33.3 | 300 | 100 | 0 | 9 |
| 24 | 33.3 | 0 | 100 | 100 | 9 |

*uc = uncontrolled

After all solutions are combined in each glass tube, the contents of each tube is poured into a tube containing coal and this tube is closed with a butyl rubber stopper, crimp-sealed with aluminum caps and incubated for 24 hours in a 50° C. water bath without shaking. Incubations are terminated by centrifuging the contents of each tube and filtering the supernatant through a Whatman GF/F glass fiber filter.

(d) Assays

Soluble total organic carbon (sTOC) in each filtered supernatant is determined on a Shimadzu TOC-V Total Organic Carbon Analyzer (Shimadzu Scientific Instruments, Columbia, Md.) by subtracting carbon dioxide evolved by acid treatment of each sample (inorganic carbon) from that detected after combustion of a specific volume on a palladium catalyst (total carbon). Total carbon and inorganic carbon values are taken as the best two of three injections values. Low, medium and high standard curves are made with the instrument auto-dilution protocol according to the manufacturer's instructions using 100, 1000 and 5000 ppm standards of potassium hydrogen phthalate (for total carbon) and sodium (bi)carbonate (inorganic carbon). Samples found to be outside of the low or medium curve are re-injected and re-measured using the next highest standard curve.

(e) Analyses

The sTOC concentration is converted from mg/l (ppm) to g/l and then to an absolute value (g) by multiplying by the total incubation volume of 0.0121. To determine the fraction of coal organic carbon solubilized, the sTOC (in g) is divided by the mass of organic carbon added to each tube based on the percent organic carbon in each coal. The percent organic carbon is determined on a dry weight basis for the lignite and sub-bituminous coals. Water gained from atmospheric water vapor during the short period between removing the coal from the drying oven and weighing is disregarded as additional weight gained from moisture prior to weighing would decrease the total coal added to each tube and increase the fraction of coal organic carbon solubilized.

Example 3

Solubilization of Lignocellulose Biomass with Pyrophosphates

Pre-steamed chips of Douglas fir at 50% moisture content are introduced into a tubular vessel at one end at a rate of 10,000 kilograms per hour. An aqueous treatment liquor having a temperature of ambient temperature, 20° C., 50° C., 100° C., 120° C., 150° C., 175° C., 200° C. or 250° C. is fed into the vessel at the other end at a rate of 5,000 kilograms per hour. Sufficient pyrophosphate to maintain a concentration of pyrophosphate in the vessel of 0.05%, 0.1%, 0.2%, 0.5%, 1%, 2.5%, 5%, 7.5%, 10%, or 20% of the lignocellulose is introduced into the vessel. Pressure in the vessel can be atmospheric pressure to 100 psi; for example, pressure can be atmospheric pressure, 50 psi, 75 psi, 100 psi, 250 psi, 300 psi, 500 psi, 750 psi or 1000 psi.

The contents of the vessel are heated by external means to a temperature of 140° C. The residence time of the wood is 10, 20, 30, 40, 50, 60 minutes, 6 hours, 12 hours, 24 hours, 2 days, 5 days, 10 days, or 30 days. Spent treatment liquor is continuously withdrawn from the vessel at the end at which the wood is introduced. The liquor which is withdrawn contains a negligible amount of pyrophosphate. The treated wood is withdrawn from the vessel at the end at which the treatment liquor is introduced.

Example 4

Solubilization of Lignocellulose Biomass with Pyrophosphates

Biomass is reacted with a water-based solution of pyrophosphate at relatively high temperatures. The effectiveness of the treatment process is studied for several different reaction conditions. Process variables studied include water loading (6 to 19 g water/g dry biomass), temperature (ambient to 200° C.) and treatment time (10 minutes to 60 minutes).

Five hundred (500)-mL glass Erlenmeyer flasks or steel vessels are used as reactors. The flasks or steel vessels are sealed and placed in a 100-rpm shaking water bath at ambient temperature or in boiling water to pre-warm them as needed to rapidly bring them to higher temperatures. Samples are agitated for the length of the treatment regimen.

Optionally, oxygen-containing gas is introduced into the reactor from a high-pressure gas container or tank attached to the system. The gas can be pure pressurized oxygen, compressed air, or any oxygen-containing gas under pressure. The pressure of the oxygen-containing gas can be determined from a pressure gauge mounted on the gas supply container or on the reactor.

Example 5

Solubilization of Lignocellulose Biomass with Pyrophosphates

About 0.24 g straw is dissolved in 150 mL water with a pyrophosphate in a concentration of about 5 mM, 20 mM, 50 mM, 100 mM, or 500 mM. The mixture is transferred into serum bottles of about 250 ml and closed with a rubber cover with an aluminum cap on top thereof. Three serum bottles are flushed with nitrogen gas (oxygen free atmosphere) and three serum bottles are flushed with air, thereby introducing oxygen. The pH is about 8.3.

These six serum bottles are subsequently transferred to an autoclave and heated to about 120° C. for two hours.

After the pre-treatment, the solid and the liquid fraction are separated.

Example 6

Solubilization of Lignocellulose Biomass with Pyrophosphates

Corn stover (0.5 g) is mixed in 150 mL water with a pyrophosphate solution (e.g., 5 mM, 20 mM, 50 mM, 100 mM, or 500 mM pyrophosphate). The mixture is incubated at 25° C., 50° C., 75° C., 100° C., 130 or 150° C. for 10 minutes, 30 minutes, 1 hour, 3 hours or 10 hours with agitation. The ionic liquid is extracted from the biomass by addition of water, centrifuged and the supernatant is removed. The solid residue is washed until 1 L is completely extracted.

Example 7

Solubilization of Lignite and Microbial Growth

A liquid extract of coal produced by solubilizing lignite with a solution of tetrasodium pyrophosphate, potassium permanganate and sodium hypochlorite supported the growth of isolate BPI090331_00181. When BPI090331_00181, a gram-negative bacterium closely related to the genus *Raoultella*, was inoculated into a medium containing coal extract, increases in both cell concentration and $CO_2$ production were observed over time. The base medium without coal extract did not support growth or significant $CO_2$ production. These results confirmed that the coal extract was not universally toxic and could be utilized as a carbon and energy source for microbial growth.

Coal Extract

Lignite coal (referred to hereafter as "BCS03") was obtained from the Wilcox formation in Mississippi. Coal extract was made by adding 170 g BCS03 with a solution of 100 mM tetrasodium pyrophosphate, 100 mM potassium permanganate and 100 mM sodium hypochlorite, adjusted to pH 9.0. The coal solution was incubated for 24 hours at 50° C., then decanted through a 100 μm nylon net filter (Millipore) and vacuum-filtered through a glass fiber filter (GF/F grade, Whatman).

Media

M9 salt solution contained, per liter in 18 MΩ water: 0.5 g sodium chloride; 11 mg calcium chloride dihydrate; 1 g ammonium chloride; 6.78 g disodium phosphate; 3 g monopotassium phosphate and 0.48 g magnesium sulfate heptahydrate.

Full-strength M9 medium was equivalent to M9 salt solution supplemented with 2.1 mg ferrous sulfate heptahydrate; 0.03 mg boric acid; 0.1 mg manganese chloride tetrahydrate; 0.19 mg cobalt chloride hexahydrate; 0.024 mg nickel chloride hexahydrate; 0.002 mg copper (cupric) chloride dihydrate; 0.144 mg zinc sulfate heptahydrate; 0.036 mg sodium molybdate dihydrate; 0.003 mg sodium selenite; 0.008 mg sodium tungstate dihydrate; 0.018 mg sodium vanadate; 0.05 mg 4-aminobenzoic acid; 0.02 mg D(+)-biotin; 0.05 mg nicotinic acid; 0.05 mg D(+)-pantothenic acid Ca-salt; 0.1 mg pyridoxine dihydrochloride; 0.05 mg thiamine hydrochloride; 0.001 mg vitamin B12; 0.02 mg folic acid; 0.05 mg thioctic acid and 0.05 mg riboflavin.

Full-strength M9 glucose medium (M9G) was the M9 medium supplemented with 1 g per liter D-glucose.

All M9 solutions and media were sterilized by filtration through 0.2 μm cellulose acetate filters (Corning).

For assays, M9 and M9G were used at 10% full strength, and called 0.1×M9 or 0.1×M9G. When supplemented with 30% coal extract, these media were called 0.1×M9XT and 0.1×M9GXT.

Cultivation

Organism BPI090331_00181 was routinely grown in Tryptic Soy Broth (TSB, Difco) at 30° C. while shaking. Seed cultures for screening were produced by growing an 8 ml primary culture of BPI090331_00181 in TSB for 24 hours. The primary culture was transferred (5 ml into 45 ml TSB) and grown for 6 hours at 30° C. This secondary culture was then concentrated by centrifuge (Sorvall RT7 Plus) at 4,000 rpm for 10 minutes and the supernatant was discarded. The cell pellet was re-suspended in M9 salts solution and centrifuged again; this procedure was repeated twice more to cleanse the cell suspension of remaining TSB medium. The optical density at 600 nm ($OD_{600\ nm}$) of the resulting suspension was determined with a 1 cm path-length on a Molecular Devices Spectramax M2$^e$ and adjusted by dilution with M9 salts to 1.0.

Ten ml of sterile media (0.1×M9, 0.1×M9G, 0.1×M9XT, or 0.1×M9GXT) were distributed into 27 ml Balch tubes and sealed under a butyl stopper with an air headspace. Six tubes were made with each medium; three of which were inoculated by addition of 0.1 ml of the 1.0 OD600 nm suspension of BPI090331_00181 cells. Tubes were placed, long edge down, in a container that was mounted on a shaker platform and incubated at 30° C. while rotating at 100 rpm.

Sampling

Headspace samples were taken by syringe and needle through the stopper immediately after inoculation and at 24, 48, 72, 168 and 216 hours post-inoculation. At each sampling, 1 ml of $N_2$ gas was introduced into the headspace and 1 ml of headspace gas was immediately withdrawn and injected into a 12-ml headspace gas vial (Agilent) containing air. A second syringe and needle was then used to withdraw 0.1 ml of liquid for cell counts.

Analyses

Cell counts were performed using a Guava flow cytometer. Cell suspensions were mixed with 1:10 with 5×SYBR® Green II dye in 0.1× phosphate-buffered saline (Invitrogen), then serially diluted 10-fold in the dye/PBS solution. Counts were collected in the green fluorescence channel; only dilutions registering in the reliable count window (between 10 and 500 events per µl) were used for calculations; these were corrected for dilution from the original sample.

Gas analyses for carbon dioxide concentration were performed on an Agilent 3000A Micro GC. Standard gas mixes were obtained from Scotty Gases (0, 0.197, 2.5, 10 and 40% $CO_2$) and 1 ml was injected into a 12 ml headspace gas vial containing air. The average GC peak areas in the 0% $CO_2$ sample were subtracted from all other standards; the resulting peak areas were linearly correlated with the standard $CO_2$ concentration ($R^2=0.9999$) permitting accurate determination of $CO_2$ above 0.2%. Calculations for gas produced in each inoculated assay tube were: (i) corrected for the amount of gas added and removed at each sampling, (ii) corrected by subtracting the $CO_2$ produced by chemical interactions alone in uninoculated tubes containing the same medium and (iii) adjusted to µmol using the lab temperature of 25° C.

Results

Figure 7:
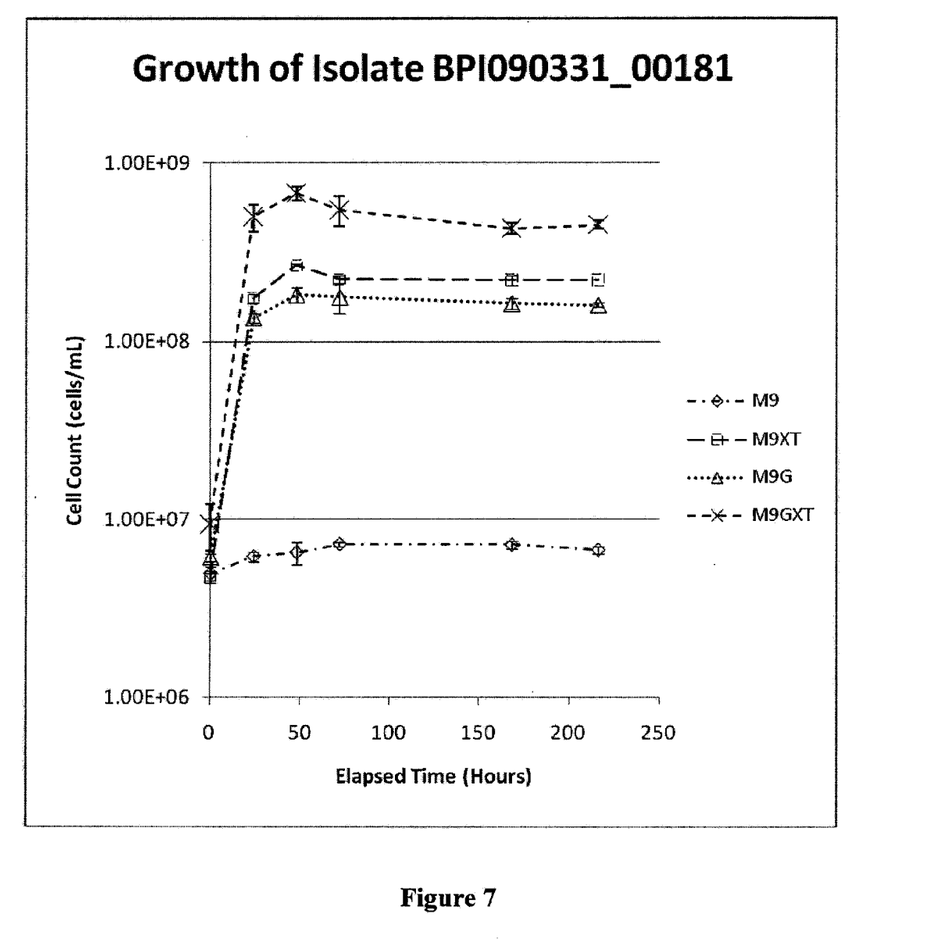
FIG. 7 illustrates observed mean cell counts (n=3) of a bacterial isolate grown on solubilized coal extract; error bars are one (1) standard deviation.
Figure 8:
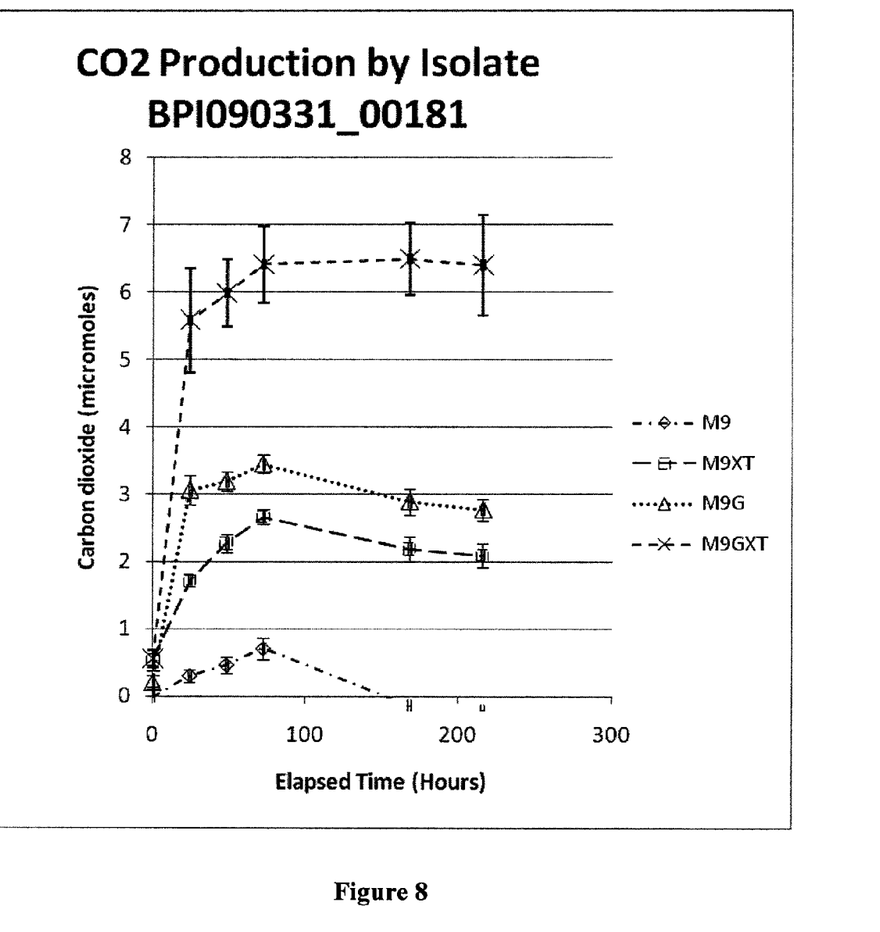
FIG. 8 illustrates observed mean $CO_2$ production for each medium (n=3) from a bacterial isolate culture grown on solubilized coal extract; error bars are one (1) standard deviation.

Cell counts (FIG. 7) and $CO_2$ concentrations (FIG. 8) increased in the presence of glucose (M9G), coal extract (M9XT) and glucose plus coal extract (M9GXT), but not significantly in M9 alone. In particular, the increased cell counts and $CO_2$ in M9XT indicate the coal extract was metabolized by isolate BPI090331_00181. Additionally, the increased cell counts and $CO_2$ production seen in M9GXT compared to M9G indicate the coal extract was not inhibitory to the growth of strain BPI090331_00181.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Normal Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

What is claimed is:

1. A method for solubilization, depolymerization or liquefaction of coal into solubilized coal products, comprising contacting coal in situ in a subterranean coal deposit with a composition comprising a pyrophosphate or a derivative thereof, and an oxidant selected from the group consisting of: hypochlorite, permanganate, and a combination of hypochlorite and permanganate, and wherein
   a) the coal is lignite coal and the contacting occurs at about pH 9;
   b) the coal is subbituminous coal, the oxidant is hypochlorite and the contacting occurs at about pH 9;
   c) the coal is subbituminous coal, the oxidant is permanganate and the contacting occurs at about pH 2 or about pH 7 or about pH 9;
   d) the coal is subbituminous coal, the oxidant is permanganate and hypochlorite, and the contacting occurs at about pH 2 or about pH 7;
   wherein said coal is solubilized.

2. The method of claim 1, wherein said pyrophosphate is sodium pyrophosphate ($NaP_2O_7$), potassium pyrophosphate ($K_4P_2O_7$), ferric pyrophosphate, pyrophosphoric acid, or a derivative thereof.

3. The method of claim 2, wherein said derivative is hexametaphosphate, sodium hexametaphosphate, potassium hexametaphosphate, calcium hexametaphosphate, sodium tripolyphosphate, disodium pyrophosphate, dipotassium pyrophosphate, tetrasodium pyrophosphate, or tetrapotassium pyrophosphate.

4. The method of claim 1, further comprising contacting said solubilized coal with one or more microorganisms, one or more consortiums, one or more functional microbial subcommunities, or one or more defined microbial assemblages.

5. The method of claim 4, wherein said one or more microorganisms, one or more consortiums, one or more functional microbial subcommunities, or one or more defined microbial assemblages comprises methanogens.

6. The method of claim 4, wherein the microorganisms comprise methanogens and methane is produced.

7. The method of claim 1 wherein the coal is lignite coal and the contacting occurs at about pH 9.

8. The method of claim 1 wherein the coal is subbituminous coal, the oxidant is hypochlorite and the contacting occurs at about pH 9.

9. The method of claim 1 wherein the coal is subbituminous coal, the oxidant is permanganate and the contacting occurs at about pH 2 or about pH 7 or about pH 9.

10. The method of claim 1 wherein the coal is subbituminous coal, the oxidant is permanganate and hypochlorite, and the contacting occurs at about pH 2 or about pH 7.

* * * * *